United States Patent
Curti (10) Patent No.: US 6,830,445 B2
(45) Date of Patent: Dec. 14, 2004

(54) NASAL AND ORAL CANNULA BREATHING DETECTION DEVICES

(75) Inventor: James N. Curti, Bakersfield, CA (US)

(73) Assignee: Salter Labs, Arvin, CA (US)

( * ) Notice: Subject to any disclaimer, the term of this patent is extended or adjusted under 35 U.S.C. 154(b) by 133 days.

(21) Appl. No.: 10/265,527

(22) Filed: Oct. 4, 2002

(65) Prior Publication Data

US 2003/0030183 A1 Feb. 13, 2003

Related U.S. Application Data

(60) Division of application No. 09/883,843, filed on Jun. 18, 2001, now Pat. No. 6,533,984, which is a continuation-in-part of application No. 09/754,471, filed on Jan. 4, 2001, now Pat. No. 6,533,983.

(51) Int. Cl.[7] .......................... B29C 41/14; B29C 41/40
(52) U.S. Cl. ...................................................... 425/275
(58) Field of Search ................................ 425/269, 270, 425/275; 249/184

(56) References Cited

U.S. PATENT DOCUMENTS

| | | | |
|---|---|---|---|
| 2,053,357 A | 9/1936 | Winder | |
| 2,296,011 A | * 9/1942 | Beal | 425/270 |
| 2,824,407 A | * 2/1958 | Ebel | 425/275 |
| 2,854,695 A | * 10/1958 | Moreau | 425/269 |
| 3,643,660 A | 2/1972 | Hudson et al. | 128/206 |
| 3,731,900 A | 5/1973 | Havstad | 249/177 |
| 3,802,431 A | 4/1974 | Farr | 128/207.18 |
| 3,906,071 A | 9/1975 | Cook et al. | 264/255 |
| 3,931,381 A | 1/1976 | Lindberg | 264/45.5 |
| 4,106,505 A | 8/1978 | Salter et al. | 128/206 |
| 4,152,688 A | 5/1979 | Dietz | 338/215 |
| 4,433,219 A | 2/1984 | Dietz | 200/83 R |
| 4,602,643 A | 7/1986 | Dietz | 128/721 |
| 4,695,241 A | 9/1987 | Ventimiglia | 425/275 |
| 4,745,925 A | 5/1988 | Dietz | 128/725 |
| 4,800,116 A | 1/1989 | Ventimiglia et al. | 428/215 |
| 4,818,320 A | 4/1989 | Weichselbaum | 156/227 |
| 4,878,502 A | 11/1989 | Dietz | 128/725 |
| 5,005,571 A | 4/1991 | Dietz | 128/205.25 |
| 5,024,219 A | 6/1991 | Dietz | 128/204.21 |
| 5,038,771 A | 8/1991 | Dietz | 128/204.21 |
| 5,046,491 A | 9/1991 | Derrick | 128/200.24 |
| 5,052,400 A | 10/1991 | Dietz | 128/722 |
| 5,074,299 A | 12/1991 | Dietz | 128/204.21 |
| 5,133,923 A | * 7/1992 | Klug | 425/275 |
| 5,335,656 A | 8/1994 | Bowe et al. | 128/207.18 |
| 5,380,182 A | 1/1995 | Packard et al. | 425/275 |
| 5,485,833 A | 1/1996 | Dietz | 128/204.23 |
| 5,485,850 A | 1/1996 | Dietz | 128/716 |
| 5,513,634 A | 5/1996 | Jackson | 128/207.18 |
| 5,682,881 A | 11/1997 | Winthrop et al. | 128/207.18 |
| 5,922,365 A | * 7/1999 | Reichner | 425/275 |
| 6,217,818 B1 | 4/2001 | Collette et al. | 264/513 |
| 6,247,470 B1 | 6/2001 | Ketchedjian | 128/200.28 |
| 6,379,312 B2 | 4/2002 | O'Toole | 600/529 |
| 6,635,214 B2 | * 10/2003 | Rapacki et al. | 264/250 |
| 2002/0171175 A1 | * 11/2002 | Ainsworth et al. | 249/184 |

FOREIGN PATENT DOCUMENTS

| | | | | |
|---|---|---|---|---|
| EP | 0 993 094 A2 | 8/1999 | | H02J/13/00 |
| RU | 1775957 C | * 9/1995 | | B29C/41/14 |
| RU | 1793628 C | * 10/1995 | | B23C/41/14 |

* cited by examiner

Primary Examiner—Robert B. Davis
(74) Attorney, Agent, or Firm—Davis & Bujold, P.L.L.C.

(57) ABSTRACT

A method of forming a cannula by forming a cannula mandrel assembly having a nare mandrel, a main body mandrel and mouthpiece mandrel; heating the cannula mandrel assembly, applying a polymeric material to the cannula mandrel assembly to provide a desired material thickness on the mandrel assembly to form the cannula, curing the polymeric material of the formed cannula and extracting the mandrel assembly from the cannula by disassembly and removal of the mandrel assembly parts.

2 Claims, 7 Drawing Sheets

NASAL AND ORAL CANNULA BREATHING DETECTION DEVICES

This application is a divisional of Ser. No. 09/883,843 filed on Jun. 18, 2001 and now U.S. Pat. No. 6,533,984 which is a continuation in part application of Ser. No. 09/754,471 filed on Jan. 4, 2001 and now U.S. Pat. No. 6,533,983.

This invention provides a novel method of producing cannulas suitable for use in both nasal and oral applications, using disconnectable mandrel parts to form the mold over which cannula forming plastics material is applied to form the cannula.

BACKGROUND OF THE INVENTION

This invention relates generally to cannulas adapted for both mouth and nasal use to monitor breathing, in particular, a method of manufacturing a cannula adapted to interconnect with both nasal passages and the mouth for use to monitor breathing, especially for the detection of apnea.

Nasal cannulas are commonly used to administer gases, such as oxygen, to humans having respiratory problems. Illustrations of nasal cannulas used for this purpose are found in U.S. Pat. No. 3,802,431. Nasal cannulas have been used also for inhalation therapy, made possible by development of inhalation sensors such as described in U.S. Pat. No. 4,745,925. A nasal cannula can be used to monitor breathing and for detection of apnea (the absence of breathing) when connected to an inhalation sensor.

Nasal cannulas additionally adapted to communicate with the mouth of humans to permit administration of fluids or sensing of apnea during periods of mouth breathing or nasal blockage are also known.

The present invention is a novel method of manufacturing a cannula to communicate with both nasal and oral passages. This method provides in the preferred embodiment, disconnectable mandrels, which when assembled form a mold over which a cannula forming polymeric material is applied, and which, through the capability of being disconnected, each mandrel part from the other(s), facilitates removal of the mandrels from the formed cannula.

The prior art of dipping a part in a plastisol to create a coating thereof is exemplified by U.S. Pat. Nos. 3,906,071, 4,695,241 and 4,800,116, the disclosures of which are hereby incorporated by reference.

SUMMARY OF THE INVENTION

It is an object of the invention to provide a method of manufacturing cannulas using an assembly of disconnectable mandrels over which cannula forming polymeric material is applied. Application of the plastics material over the mandrel assembly and subsequent extraction of the mandrel sections following curing of the cannula material provides a finished cannula with contiguous internal flow paths to monitor a patent's breathing.

It is a further object of the invention to provide a multipart mandrel assembly for forming a cannula which facilitates extraction of the mandrel assembly sections after at least partial curing the polymeric material forming the cannula.

Still another object of the invention is to form the main body forming mandrel as two separate, slightly spaced apart components which remain spaced apart from one another by a void, during the dipping process, so that the void becomes filled with a plastisol to form a septum or barrier which divides the internal passage into two compartments or passageways, one which facilitates the supply of supplemental oxygen to a patient while the other facilitates monitoring of the breathing of the patient.

According to the invention, there is provided a method of forming a cannula comprising separable parts including the steps of providing a cannula mandrel assembly, said assembly comprising at least one nare forming mandrel, at least one mouthpiece forming mandrel, and a main body forming mandrel; heating the cannula mandrel assembly to a desired temperature; providing an uncured cannula forming polymeric material in flowable state; applying at least one coating of the material to the cannula mandrel assembly to provide a desired coating material thickness on the cannula mandrel assembly to form the cannula; at least partially curing the material coating the cannula mandrel assembly; and disassembling the cannula mandrel assembly and withdrawing the at least one nare forming mandrel, and the at least one mouthpiece forming mandrel and the main body forming mandrel from the cannula.

Also according to the invention there is provided a method of forming a cannula comprising the steps of providing cannula mandrel assembly parts, said parts comprising a pair of nare forming mandrels, a main body forming mandrel having a central rectangular recessed section and openings to receive and engage ends of the nare forming mandrels, and a mouthpiece forming mandrel having an end connector, the end connector defining a slot dimensioned to mate slidingly with the rectangular recessed section; assembling the parts to provide a cannula mandrel assembly defining interior spaces of the cannula; heating the cannula mandrel assembly to a desired temperature; providing a cannula forming polymeric material as a plastisol; dipping the heated cannula mandrel assembly in the plastisol to provide a desired thickness of partially cured polymer on the cannula mandrel assembly to form the cannula; heating the cannula material of the cannula to further cure the cannula material; and extracting the nare forming mandrels, the mouthpiece forming mandrel by removing the slot from the rectangular recess, and the main body forming mandrel from the cannula.

Also according to the invention there is provided a method of forming a cannula comprising the steps of a) providing parts for a cannula mandrel assembly comprising a nare forming mandrel, a main body forming mandrel and a mouthpiece forming mandrel having an end connector to slidably engage the main body forming mandrel; b) removably mounting the nare forming mandrel to the main body forming mandrel to provide a desired orientation of the nare forming mandrel relative to the main body forming mandrel and slidably engaging the connector with the main body forming mandrel to provide a desired orientation of the mouthpiece forming mandrel relative to the nare forming mandrel and the main body forming mandrel to form the cannula mandrel assembly; c) heating the cannula mandrel assembly to a desired temperature; d) dipping the heated cannula mandrel assembly into a plastisol of a polymeric material to provide a desired thickness of polymeric material on the cannula mandrel assembly to form the cannula; e) at least partially curing the polymeric material; f) extracting the nare forming mandrel, the mouthpiece forming mandrel, and the main body forming mandrel from the cannula by reversing the assembly steps of subparagraph b).

Also according to the invention there is provided a cannula mandrel assembly, defining the interior cavity of a cannula having a main body, a nare and a mouthpiece, comprising an elongate nare forming mandrel; an elongate mouthpiece forming mandrel; and an elongate main body forming mandrel defining a recessed rectangular section slidably receiving, engaging and supporting a connector end feature of the mouthpiece forming mandrel and defining a transverse opening receiving, engaging and supporting an end of the nare forming mandrel.

BRIEF DESCRIPTION OF THE DRAWINGS

The invention will now be described, by way of example, with reference to the accompanying drawings, in which.

DETAILED DESCRIPTION OF THE EMBODIMENTS

Figure 1:
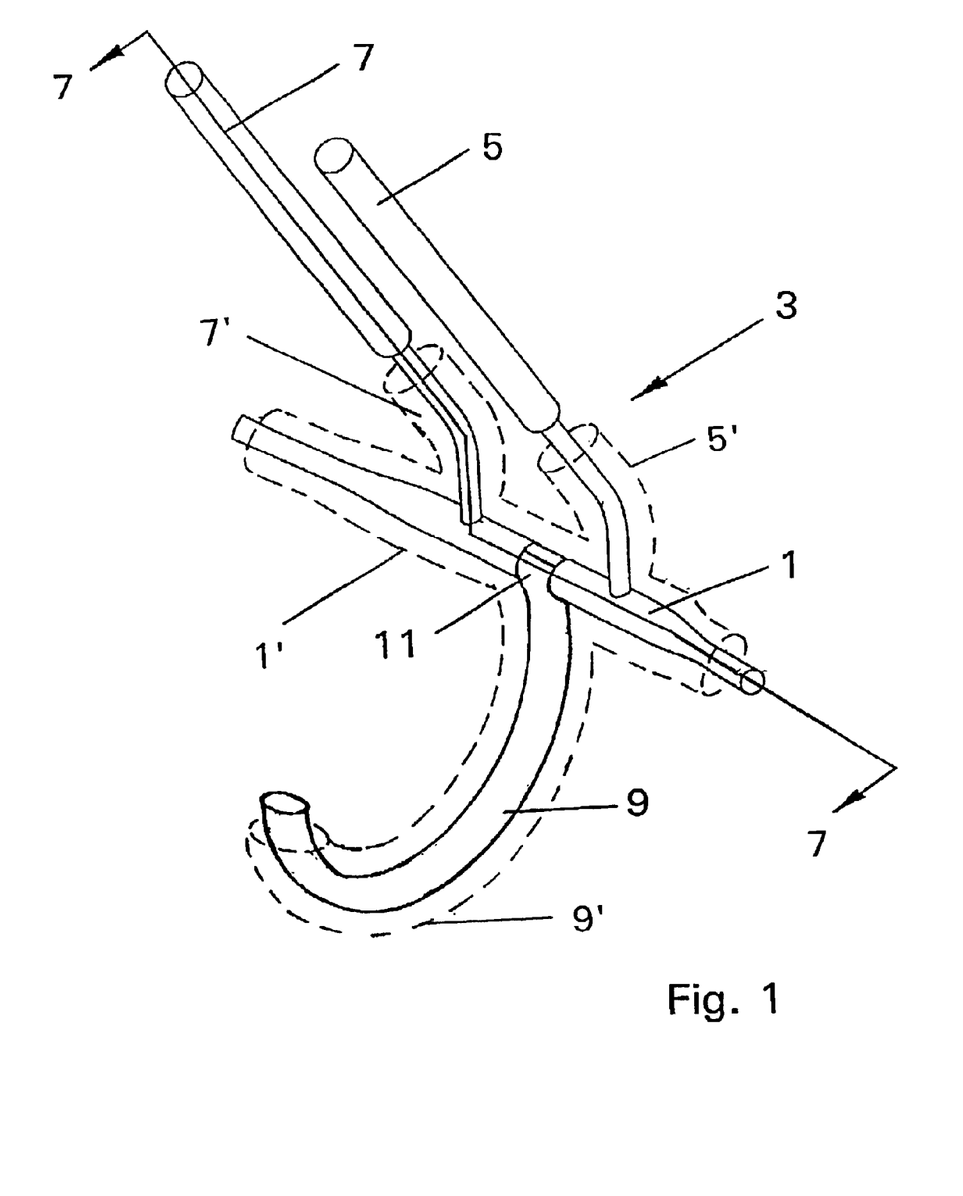
FIG. 1 is an orthogonal view of a cannula mandrel assembly with cannula forming polymeric material shown in ghost.

Referring to FIG. 1, the main body forming mandrel 1 of a beryllium copper cannula mandrel assembly 3 is shown with nare forming mandrels 5 and 7, and a mouthpiece forming mandrel 9 with end connector 11, for joining the mouthpiece mandrel 9 to the main body forming mandrel 1. Shown in ghost is a cannula formed on the assembly and comprising a main body 1', a pair of nares 5', 7' and a mouthpiece 9' composed of polyvinyl chloride (PVC).

Figure 2:
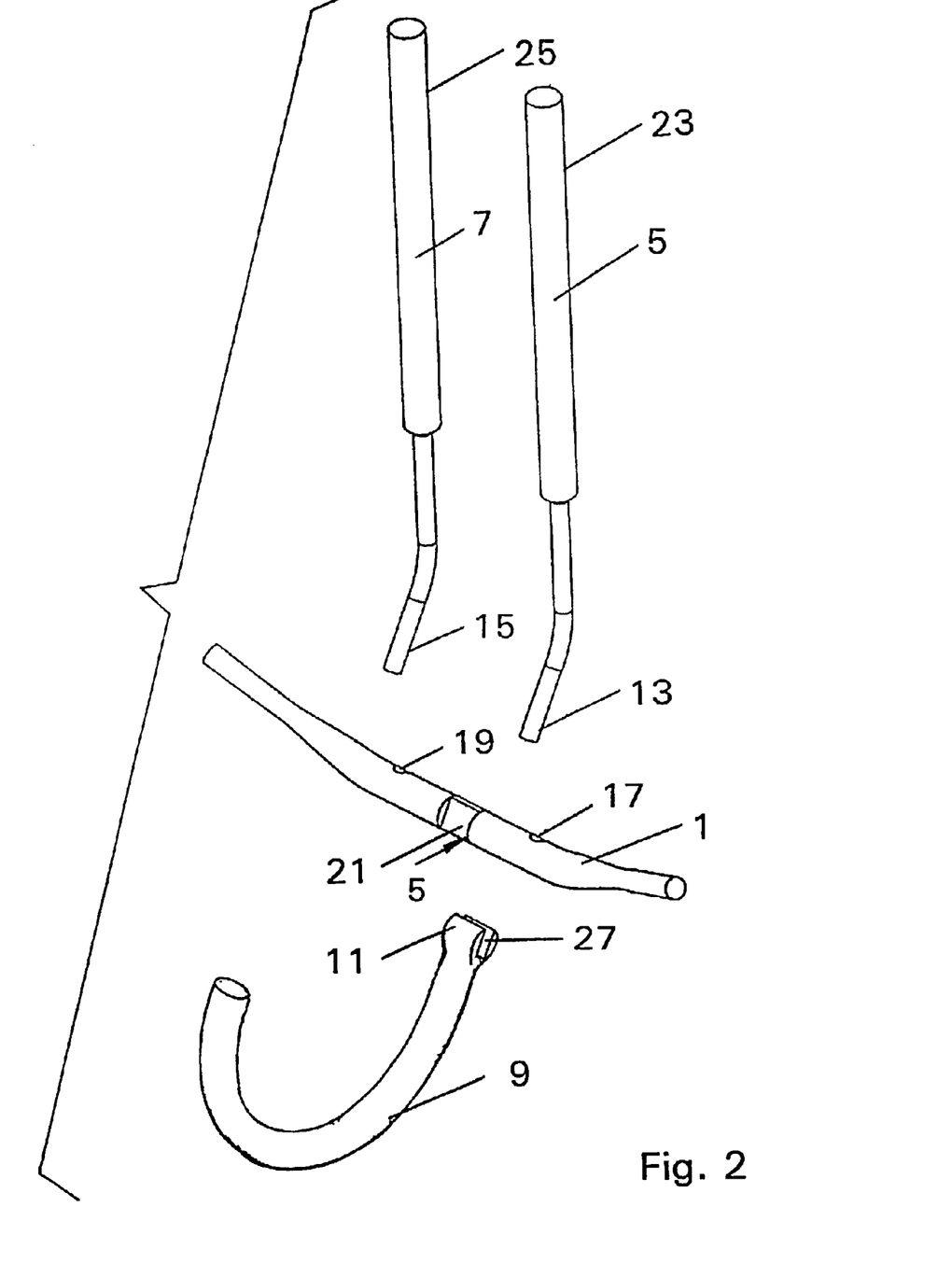
FIG. 2 is an orthogonal view of the cannula mandrel parts prior to assembly.

FIG. 2 shows the mandrel assembly parts prior to assembly to produce the cannula mandrel assembly 3. Nare mandrels 5 and 7 have reduced diameter sections 13 and 15 to form nares 5', 7', respectively, over which cannula material is applied. Reduced diameter sections 13 and 15 of nare mandrels 5 and 7 mate slidably with blind holes 17 and 19 of main body mandrel 1. Main body mandrel 1 also has a rectangular recessed section 21 to slidably mate with end connector 11 of mouthpiece mandrel 9.

Nare mandrels 5 and 7 also have enlarged diameter sections 23 and 25 to support the mandrel in a jig. Additionally, the enlarged diameter enables sections 23 and 25 to provide a larger contact surface to provide grip for removal of nare mandrels 5 and 7 from main body mandrel 1 after partial curing of the PVC on mandrel assembly 3.

FIG. 2 further shows the mouthpiece mandrel 9 with the end connector 11 which has a slot 27 to slidably engage the rectangular section 21 of the main body mandrel 1. Slot 27 is sized to permit close contact of slot 27 with the rectangular section 21 of main body mandrel 1 such that a snug fit is obtained to removably retain the mouthpiece mandrel 9 on the main body mandrel 1 while facilitating extraction from rectangular section 21 following partial curing and cooling of the PVC. The outer surface of end connector 11 approximates the outer diameter of main body mandrel 1 to provide a uniform diameter of applied cannula material and to facilitate withdrawal of the mouthpiece mandrel 9 from the mouthpiece 9' of the cannula.

Figure 3:
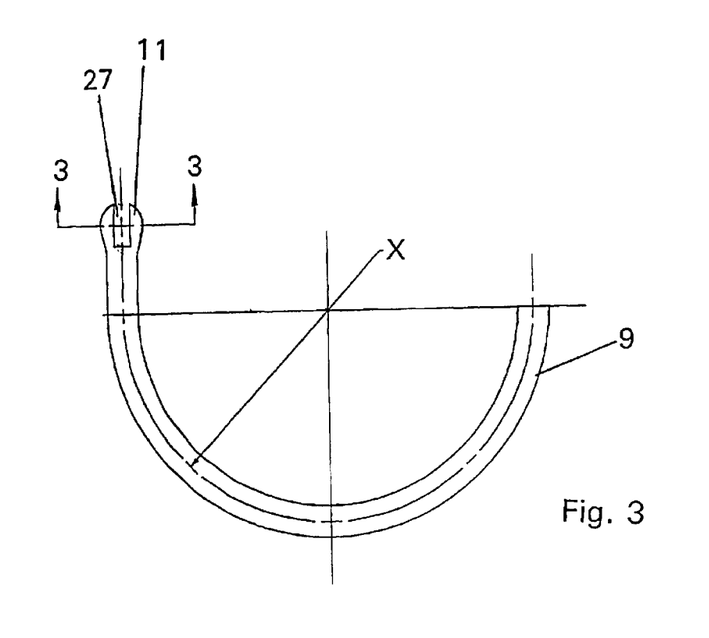
FIG. 3 is a side elevation of the mouthpiece mandrel of FIGS. 1 and 2 showing an end connector.

FIG. 3 shows mouthpiece mandrel 9 having a desired radius X and end connector 11 with slot 27.

Figure 4:
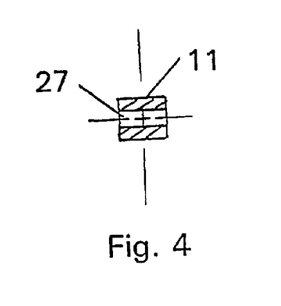
FIG. 4 is an end section of the end connector taken on section 3—3 of FIG. 3.

FIG. 4 shows the shape of end connector 11 and slot 27 through section 3—3 of FIG. 3.

Figure 5:
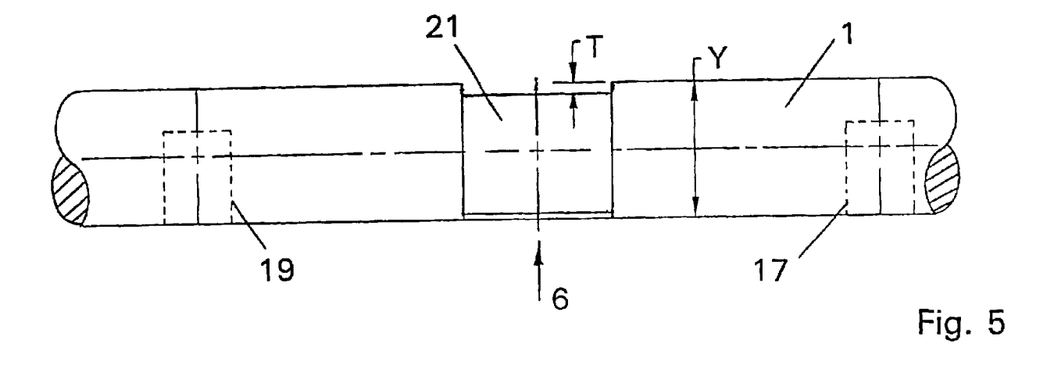
FIG. 5 is a fragmentary side elevation of the main body mandrel of FIGS. 1 and 2 taken in the direction of arrow 5 in FIG. 2.
Figure 6:
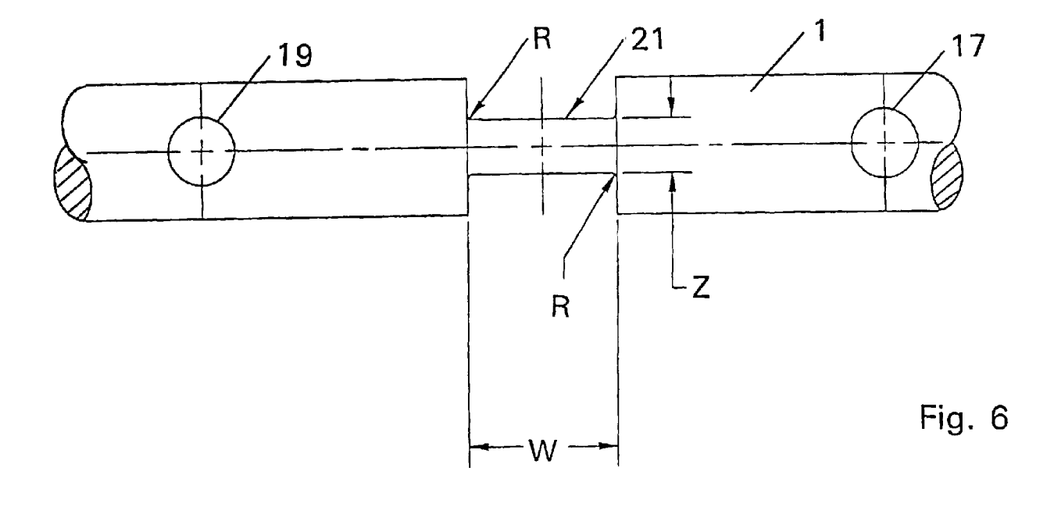
FIG. 6 is an elevation of the main body mandrel taken in the direction of arrow 6 in FIG. 5.

Referring to FIGS. 5 and 6, blind holes 17 and 19 are sized to mate slidably with reduced diameter sections 13 and 15 of the nare mandrels 5 and 7 in order to engage and support nare mandrels 5 and 7 during application of the PVC to form the cannula on the assembly 3. The rectangular section 21 is made with shoulder depth T removed to allow the diameter of end connector 11 of mouthpiece mandrel 9 to mate approximately flush with the diameter Y of main body 1.

Rectangular section 21 is shown with preferred relieving radii R at opposed ends of the section. Radius R may be omitted if main body mandrel 1 is machined or formed in a manner that allows this. Thickness Z of rectangular section 21 permits slot 27 of end connector 11 of mouthpiece mandrel 9 to firmly but slidably mate with rectangular section 21. Width W of rectangular section 21 is just sufficient to closely accommodate end connector 11 of mouthpiece mandrel 9.

FIGS. 1 and 2 show nare mandrels 5 and 7 with bend sections. These bend sections direct the nares of the cannula into a patient's nasal cavities.

Although beryllium copper is the preferred material for the cannula mandrel assembly 3, other materials which possess appropriate working temperature ranges, retain dimensional stability for reuse in a manufacturing environment and which will release the cannula easily after curing of the PVC may be used. Metals including but not limited to the steels, aluminum, bronze, brass, and copper alloys may be used, as well as some plastics. Beryllium copper is preferred due to its ability to transfer heat rapidly and reliably release the cured plastics material of the cannula formed thereon. Rapid heat transfer is desirable for the mandrel material, both during heating cannula mandrel assembly 3 and following cannula material application, when a partial cure of the material is followed by rapid cooling.

Prior to application of a latex solution of PVC (plastisol) the cannula mandrel 3 is coated, usually by dipping, with a silicone release layer to facilitate removal of the mandrel from the plastisol to be applied. The application of the PVC in the preferred embodiment is by dipping the silicone coated cannula mandrel assembly 3 which has been heated in an oven at an oven temperature of from about 350° F. to about 550° F. (preferably about 450° F.) for about 1 to about 3 minutes into a latex solution of PVC (plastisol). One or more dipping steps may be performed to achieve the desired finished cannula material thickness and each of these dipping steps may be for 10–30 seconds. During dipping the mandrel is supported by the outer end portions of the nare mandrels.

The preferred use of a latex solution of PVC (plastisol) provides a semi-clear finished cannula with strength to withstand attachment of connectors and flexibility to prevent injury to the user. Alternatively, other plastics materials, which provide material properties suitable for this method, capable of forming a plastisol may be substituted for PVC,.

Partial curing of the cannula takes place on the mandrel assembly 3. The cannula mandrel assembly with the partially cured PVC thereon is then placed in an oven a sufficient time for further curing at a temperature from about 410° F. to about 450° F. Following curing to stabilize the PVC and after the cannula has cooled sufficiently to allow mandrel removal with the assistance of the release layer, without damaging the cannula, while providing sufficient physical strength to retain cannula shape, the mandrel parts are removed from the cannula.

Using the inventive method, a cannula with two nares and a mouthpiece is formed as follows: a cannula mandrel assembly 3 is formed by first, slidably mating reduced diameter sections 13 and 15 of nare mandrels 5 and 7 with blind holes 17 and 19, respectively, of the main body mandrel 1; second, orienting nare mandrels 5 and 7; third, slidably mating slot 27 of end connector 11 of the mouthpiece mandrel 9 with the rectangular section 21 of main body mandrel 1 in a desired orientation relative to nare mandrels 5 and 7; fourth, providing a silicone release layer substantially encompassing the mandrel; fifth, heating the assembled cannula mandrel assembly in an oven at a temperature of from about 350° F. to about 550° F.; sixth, providing a liquid uncured latex PVC mix (plastisol); seventh, dipping the cannula mandrel assembly into the plastisol, at least once, until the desired material thickness on the assembly is achieved; eighth, at least partially curing the PVC at a temperature of about 410° F. to from about 450° F.; and ninth, removing the nare mandrels 5 and 7 from the blind holes 17 and 19 of main body mandrel 1 and the nares 5', 7' by pulling on enlarged diameter sections of nare mandrels 5 and 7, removing mouthpiece mandrel 9 from the mouthpiece 9' by disconnecting slot 27 of end connector 11 from rectangular section 21 of main body mandrel 1 and pulling the mouthpiece mandrel 9 through the mouthpiece 9'; and finally slidably removing main body mandrel 1 from the main body 1' of the cannula.

Figure 7:
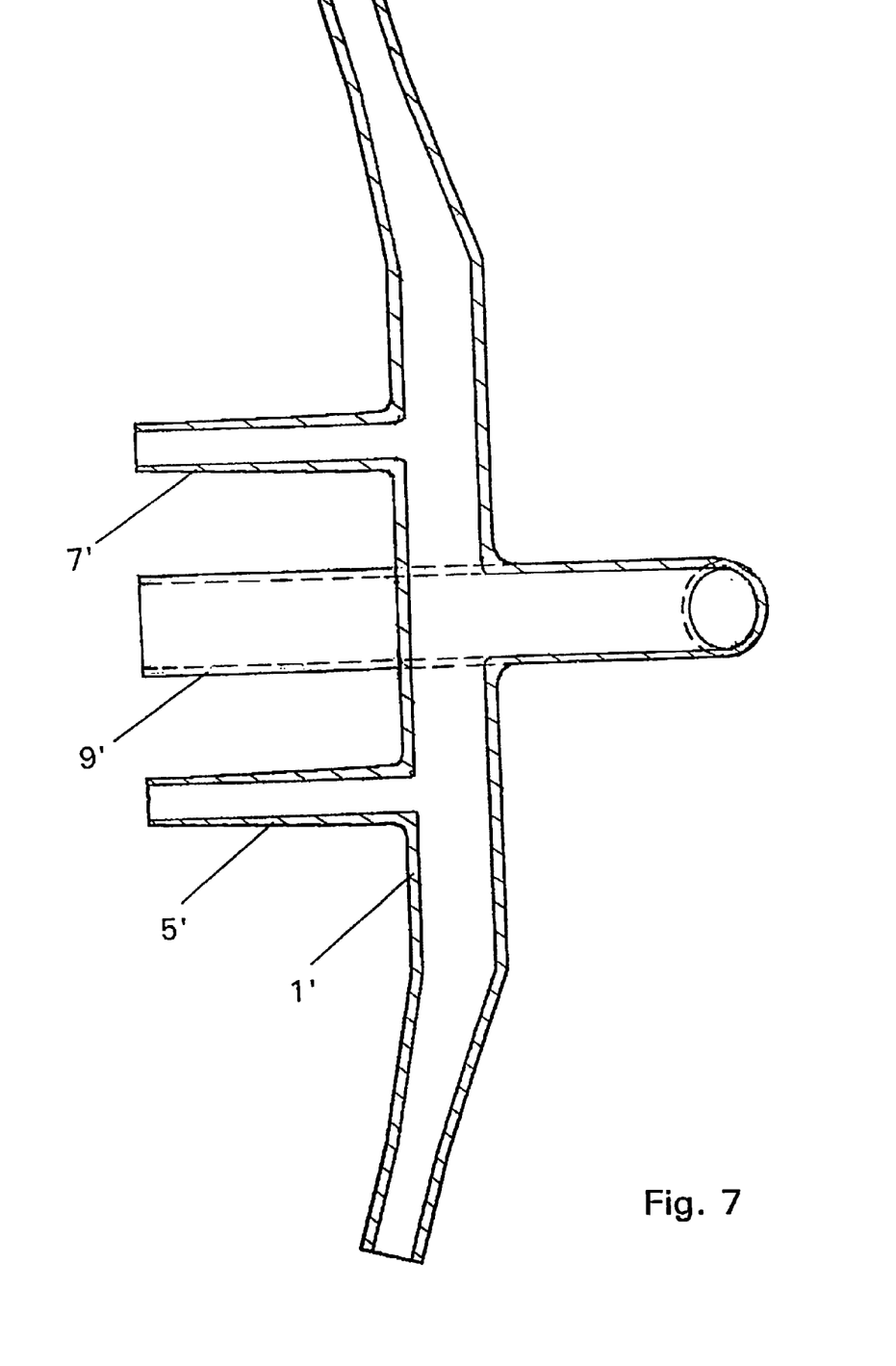
FIG. 7 is a general cross-section of a cannula made by the method of the present invention taken in the direction of section 7—7 of FIG. 1.
Figure 8:
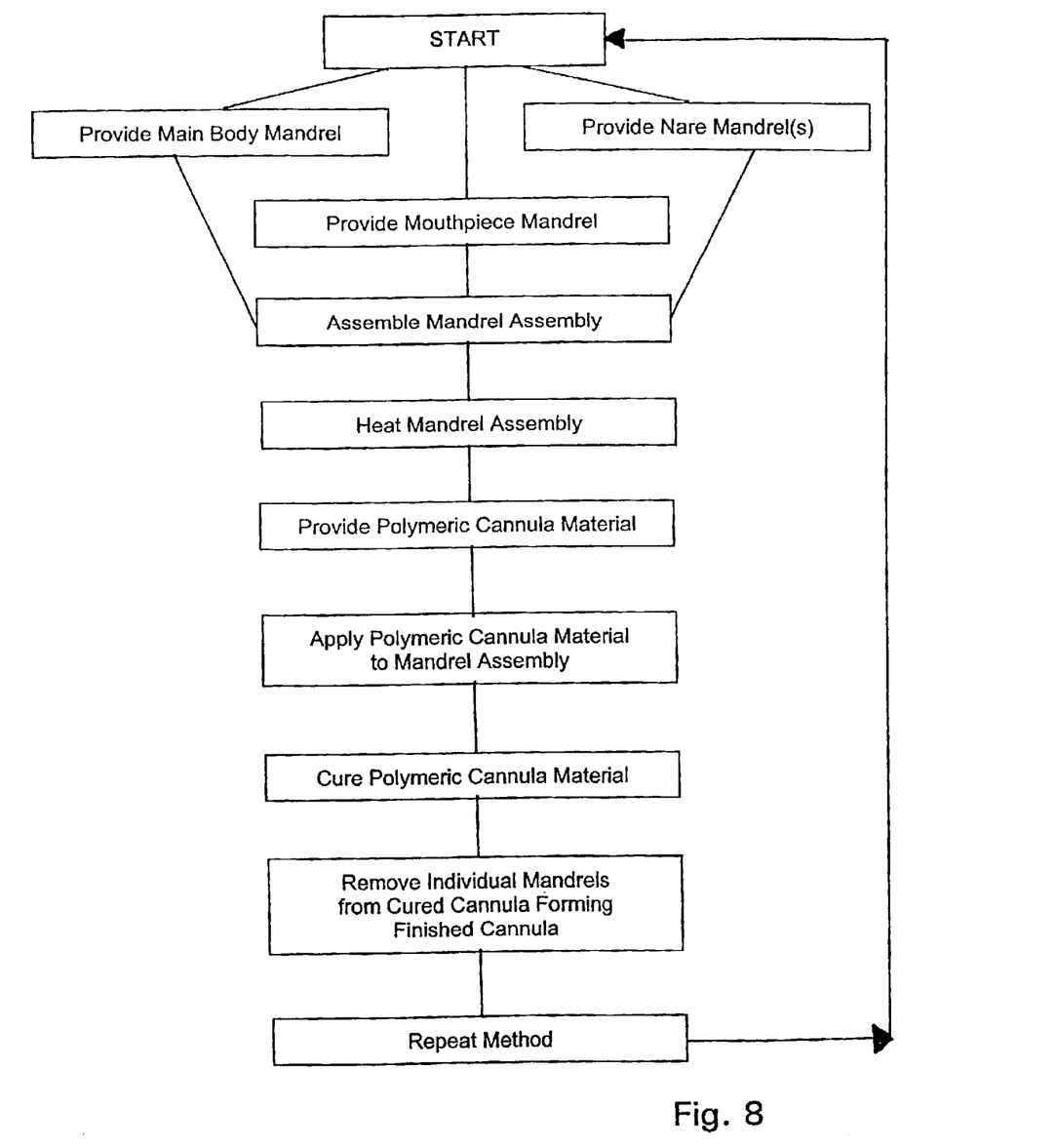
FIG. 8 is a flow diagram of the method of the present invention.

FIG. 7 show a finished cannula, following removal of cannula mandrel assembly 3 parts from the cured PVC, showing contiguous flow paths through the main body 1', nares 5' and 7' and mouthpiece 9'.

It will be appreciated that the curing step may be completed in two stages, a first partial cure of the PVC produced by the heated cannula mandrel assembly 3 sufficient to maintain the PVC on this assembly and a second step in an oven at the above curing temperatures to complete the curing of the PVC.

It will be further appreciated that the outer ends of the main body 1' may be trimmed to provide a discrete area where connecting tubing may be connected thereto, e.g. by solvent bonding, and that the mouthpiece may be trimmed to a length suited to an individual patient so as to maximize the sensitivity of the finished device.

It will also be understood that disassembly of the cannula mandrel assembly, following cannula material cure, can proceed by removing the mouthpiece mandrel before the nare mandrels as obvious alternative method steps, prior to removal of the main body mandrel.

Figure 9:
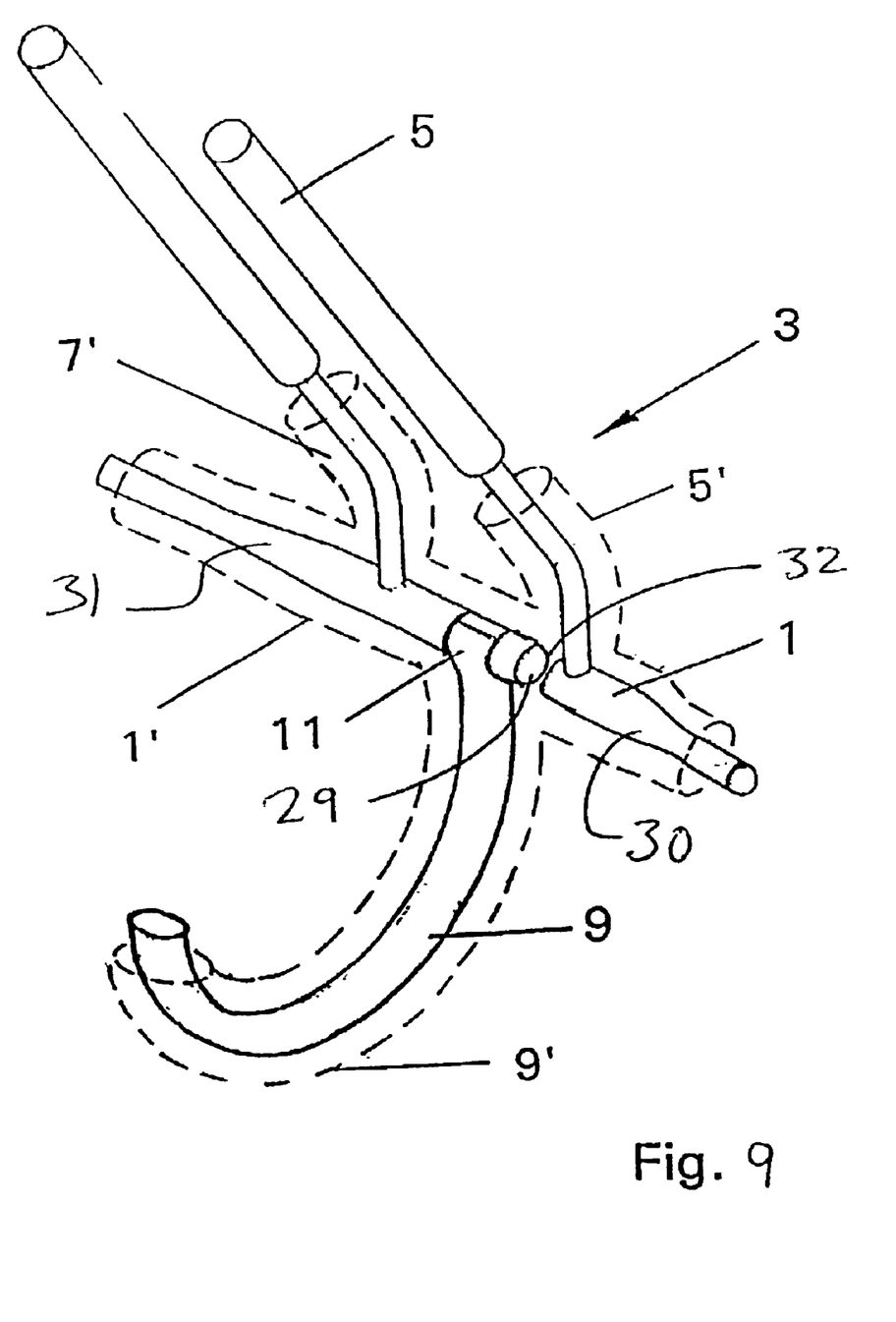
FIG. 9 is an orthogonal view of a cannula mandrel assembly for forming a septum or barrier in a void of the main body forming mandrel, with cannula forming polymeric material shown in ghost.

One modification of the present invention relates to the addition of a septum in the internal passage of the cannula to provide a barrier therein. The septum 29 divides the internal passage into two compartments or passageways so that a first one of the nares 5' can be coupled to an oxygen source (not shown) to facilitate the supply of supplemental oxygen to one of the nostrils of a patient while the other one of the nares 7' and the central mouthpiece 9' can be coupled to a monitoring device (not shown), such as a transducer, to facilitate monitoring of breathing of the patient or coupled to a demand oxygen conserving device (not shown) while the patient, at the same time, is still able to receive, either continuously or intermittently during the sensed breathing cycle, a supply of oxygen.

To manufacture the septum 29, the main body forming mandrel 1 is formed as first and second separate, slightly spaced apart components 30, 31 which remain spaced apart from one another by a void 32 during the dipping operation of the manufacturing process so that the void 32 between the first and second separate, slightly spaced apart components 30, 31 is filled with the plastisol to form the septum 29. Once the cannula is cured, the septum 29 forms a barrier which divides the internal passage into two compartments or passageways. This variation of the manufacturing process is suitable for intermittent nocturnal oxygen delivery even though the patient breaths through his or her mouth.

| Reference numerals | |
|---|---|
| 1 | main body mandrel |
| 1' | main body |
| 3 | cannula mandrel assembly |
| 5 | nare mandrel |
| 5' | nare mandrel |
| 7 | nare mandrel |
| 7' | nare |
| 9 | mouthpiece mandrel |
| 9' | mouthpiece |
| 11 | end connector |
| 13 | reduced diameter section |
| 15 | reduced diameter section |
| 17 | blind hole |
| 19 | blind hole |
| 21 | rectangular recessed section |
| 23 | enlarged diameter section |
| 25 | enlarged diameter section |
| 27 | slot |
| R | radius |
| T | rectangular section shoulder depth |
| W | rectangular section width |
| X | mouthpiece mandrel radius |
| Y | main body diameter |
| Z | rectangular section thickness |

I claim:

1. A cannula assembly, defining an interior cavity of a cannula having a main body, first and second nares and a mouthpiece, comprising:
    a first elongate nare forming mandrel;
    a second elongate nare forming mandrel;
    an elongate mouthpiece forming mandrel; and
    an elongate main body forming mandrel defining a recessed rectangular section slidably receiving, engaging and supporting a connector end feature of the mouthpiece forming mandrel and defining a transverse opening receiving, engaging and supporting an end of one of the first and second nare forming mandrels, and the elongate main body forming mandrel comprising two separate components defining a void therebetween for forming a septum.

2. The assembly according to claim 1, wherein an end of each of the first and second the nare forming mandrels are received, engaged and supported by respective ones of two openings disposed one on each side of the recessed rectangular section.

* * * * *